United States Patent [19]
Mussi et al.

[11] Patent Number: 5,583,037
[45] Date of Patent: Dec. 10, 1996

[54] TRANS-MEMBRANE CO-CULTURE INSERT AND METHOD FOR USING

[75] Inventors: Edward F. Mussi, Hewitt, N.J.; William A. Macchi, Sarasota, Fla.

[73] Assignee: Becton, Dickinson and Company, Franklin Lakes, N.J.

[21] Appl. No.: 413,293

[22] Filed: Mar. 30, 1995

[51] Int. Cl.$^6$ .............................. C12N 5/00; C12M 3/06
[52] U.S. Cl. .............................. 435/240.241; 435/297.1; 435/297.5; 422/101
[58] Field of Search .............................. 435/240.1, 240.2, 435/240.23, 240.241, 297.1, 297.5; 422/101; 210/435, 445, 446, 455, 472, 473, 476, 482

[56] References Cited

U.S. PATENT DOCUMENTS

| | | | |
|---|---|---|---|
| 1,032,917 | 7/1912 | Lynch | 210/482 |
| 2,110,237 | 3/1938 | Parsons | 422/101 |
| 3,221,878 | 12/1965 | Brett | 435/297.1 |
| 4,783,318 | 11/1988 | Lapakko | 422/101 |
| 5,272,083 | 12/1993 | Butz et al. | 435/297.5 |
| 5,409,829 | 4/1995 | Mussi et al. | 435/240.241 |
| 5,470,743 | 11/1995 | Mussi et al. | 435/297.1 |

FOREIGN PATENT DOCUMENTS

| 14225 | 8/1887 | United Kingdom | 210/482 |
|---|---|---|---|

Primary Examiner—William Beisner
Attorney, Agent, or Firm—Arthur D. Dawson

[57] ABSTRACT

An insert for trans-membrane co-culture includes a hollow housing with a passageway therethrough, a first end, a second end and a center section intermediate the first and second end. The passageway has an inside diameter at the first end and the second end that is larger than the inside diameter of the passageway at the center section so that the passageway tapers from each end to the center section. The center section includes a porous membrane having a first surface and a second surface attached across and obstructing the passageway. The membrane forms a first receptacle from the passageway toward the first end and forms a second receptacle from the passageway toward the second end. A method for using the insert of the present invention to grow cells on both sides of a porous membrane includes horizontally submerging the insert in liquid medium so that the air in the receptacles is displaced by the medium. The insert is then tipped to an upright position while maintaining one end below the surface of the liquid. The insert is stood upright on the bottom of the well and a first cell suspension introduced in to the first receptacle. After allowing the first cell suspension to form a layer of cells on the first surface of the membrane the insert is removed, drained and again horizontally immersed in liquid medium so that the receptacles are filled. The insert is then returned to vertical while maintaining the first end below the surface of the medium, stood on the first end and a second cell suspension is introduced into the second receptacle. After suitable incubation, the second cell population forms a layer on the second surface of the membrane.

15 Claims, 7 Drawing Sheets

TRANS-MEMBRANE CO-CULTURE INSERT AND METHOD FOR USING

FIELD OF INVENTION

This invention generally relates to the trans-membrane co-culture of cells. More particularly the invention relates to a two receptacle cell-culture insert with the receptacles separated by a microporous membrane and a method for its use in culturing cells.

BACKGROUND

Culturing of cells of various types has become a routine process in many laboratories. Cells are grown to harvest compounds, to test for various sensitivities to potentially toxic compounds and even to provide tissue for grafts. This work generally is a monoculture, i.e., cells of one type are grown in a suitable medium.

More recently, interest has developed in the co-culture of cells. Co-culture of cells involves growing one population of cells in the presence of another population of cells. Co-culture of cells is important for study of inflammation reactions, cell differentiation processes and blood brain permeability studies.

Representative literature reports related to cell co-culture include: Magnum et al., *In Vitro Cell Dev. Biol.* 26:1135–1143 (Dec. 1990), "Co-Culture of Primary Pulmonary Cells to Model Alveolar Injury and Translocation of Protein"; Madara et al., *J. Tissue Cult. Method,* 14:209–216, (1992), "A Simple Approach to Electrical Parameters of Cultured Epithelial Monolayers: Use in Assessing Neutrophil-Epithelial Interactions"; Miller et al., *J. Tissue Cult. Method,* 14:217–224, "Application of Cultured Endothelial Cells of the Brain Microvasculature in the Study of the Blood-Brain Barrier"; and *Science,* 266:564–565 (1995), "Finding Clues About How Embryo Structures Form." The above referenced articles are cited to provide background regarding the in vitro study of interaction between one cell type and another.

Miller et al., cited above, describes culturing of cells on solid plastic surfaces and filters or membrane inserts. Miller et al. reports that bovine brain endothelial cells (BBEC) cultured on filters or membrane inserts provides an advantage over BBEC cultured on solid plastic surfaces. This advantage is that cell polarity with respect to metabolism or receptor distribution can be examined. Miller et al. further states that BBEC culture on filters or membrane inserts are required for determining the trans cellular transport or permeability of a compound across the cellular monolayer.

The above referenced *Science* article describes work done on kidney development. The article reports Mesenchymal cells co-cultured with cells producing Wnt-1 protein differentiate into kidney structures, including nephron tubular and glomular tissue and reports that this effect is not seen with control cells.

In response to the developing need for devices and equipment to co-culture cells, a co-culture system is disclosed in the commonly assigned U.S. patent application Ser. No. to Mussi et al. 08/124,415, now U.S. Pat. No. 5,409,829. The disclosure provides a complete self-contained system for preparing a co-culture of cells.

U.S. Pat. No. 5,026,649 to Lyman et al. discloses an insert device that can be utilized to culture and co-culture cells. U.S. Pat. No. 4,871,674 to Matsui et al. discloses an insert for culturing cells having a porous membrane forming the bottom of a cylinder. The cylinder additionally has provisions for being suspended in a well.

Both the Lyman et al. disclosure and the Matsui et al. disclosure can be used to culture cells on a membrane, but neither is well suited for growing populations of cells on opposite sides of a membrane. The cell culture system disclosed in U.S. patent application Ser. No. 08/124,415 is well suited to culture cells on both sides of a membrane, but requires a series of manipulations that may be time consuming for screening studies where multiple co-cultures are being developed.

Additionally, there are reports in the literature suggesting that it is desirable to substantially eliminate air bubbles on the underside of the membrane during cell growth on the top side of the membrane, because uniform cell growth on the membrane top surface is inhibited on membrane regions having bubbles on the underside. Removal of bubbles from the underside of the membrane may prove difficult with the referenced devices.

In view of the increasing interest in co-culture of cells, there is a need for a simple to use apparatus for co-culture of cells that enables the practitioner to substantially avoid air bubbles on the underside of the membrane. Such a device and a method for it use is described herein below.

SUMMARY

A trans-membrane cell culture insert includes a hollow housing with an axial passageway therethrough, a first end, a second end and a center section intermediate the first end and the second end. The passageway at the first end and the second end of the tube has inside diameters greater than an inside diameter of the passageway at the center section so that the passageway tapers from each end to the center section. The center section further includes a porous membrane with a first surface and a second surface. The membrane is fixedly attached across and obstructs the passageway so that a first receptacle is formed from the passageway toward the first end by the first surface of the membrane and a second receptacle is formed from the passageway toward the second end by the membrane second surface.

A method for using the insert of the present invention includes submerging the insert with the axis substantially horizontal in a first well containing sufficient liquid cell growth medium to cover the insert with the membrane substantially perpendicular to the axis and both receptacles filled with medium without air bubbles. The insert is then tipped to a position where the axis is substantially vertical while maintaining the second end below the surface of the medium so that the second receptacle is filled with medium and has no air bubbles. The insert is then stood on its second end in the well so that the first surface of the membrane is upward. The levels of medium in the first receptacle and in the first well are then adjusted so that a sufficient volume of medium is present in the well for culturing cells and the insert stands upright in the first well. The method then includes introducing a first cell suspension into the first receptacle and incubating the first well with the insert therein so that the cells of the first suspension form a growth on the first surface of the membrane. The insert is then removed from the first well and the first receptacle is drained leaving the first cell growth on the first surface of the membrane. The method then includes submerging the insert substantially horizontally in a well containing sufficient liquid growth medium to cover the insert. When the insert is submerged axially horizontally, the membrane is substantially perpendicular to the axis and the receptacles fill with medium without air bubbles. The insert is then tipped to a vertical position while maintaining the first end below the surface of the medium so that the first receptacle is filled with medium without air bubbles. The insert is then stood on its first end so that the second surface of the membrane is upward and the volume of medium in the second receptacle and the well is adjusted so that sufficient medium is present in the second receptacle for culturing cells and the insert stands in the well. A second cell culture suspension is then introduced into the second receptacle and the well with the insert is incubated so that the cells of the second suspension form a growth on the second surface of the membrane.

The insert and method of the present invention provide a simple, easy to use device and technique useful for growing cell populations on both sides of a porous membrane. Cell populations grown in this fashion develop structures useful for modeling the blood/brain barrier, studies of organ development and the like. The cellular differentiation seen using the insert and method of the present invention previously was difficult to duplicate in vitro. The tapering walls of the receptacles allow substantially all air to be displaced by medium when the insert is horizontally submerged avoiding problems of cell growth inhibition attributed to air bubbles on the lower surface of the membrane.

DETAILED DESCRIPTION

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Referring to FIGS. 1, 2, 3a and 3b, a trans-membrane co-culture insert 10 of the present invention includes a hollow housing 12 with a passageway 14 having a longitudinal axis A therethrough. Insert 10 has a first end 16 and a second 18 with a center section 20 intermediate the first end and the second end. Passageway 14 has an inside diameter "a" at the first end and an inside diameter "b" at the second end. Preferably the inside diameters at each of the ends are greater than an inside diameter "c" of center section 20 so that passageway 14 forms a taper 22 from each end to the center section. Preferably, inside diameter "a" at first end 16 is substantially equal to inside diameter "b" at second end 18.

Figure 1:
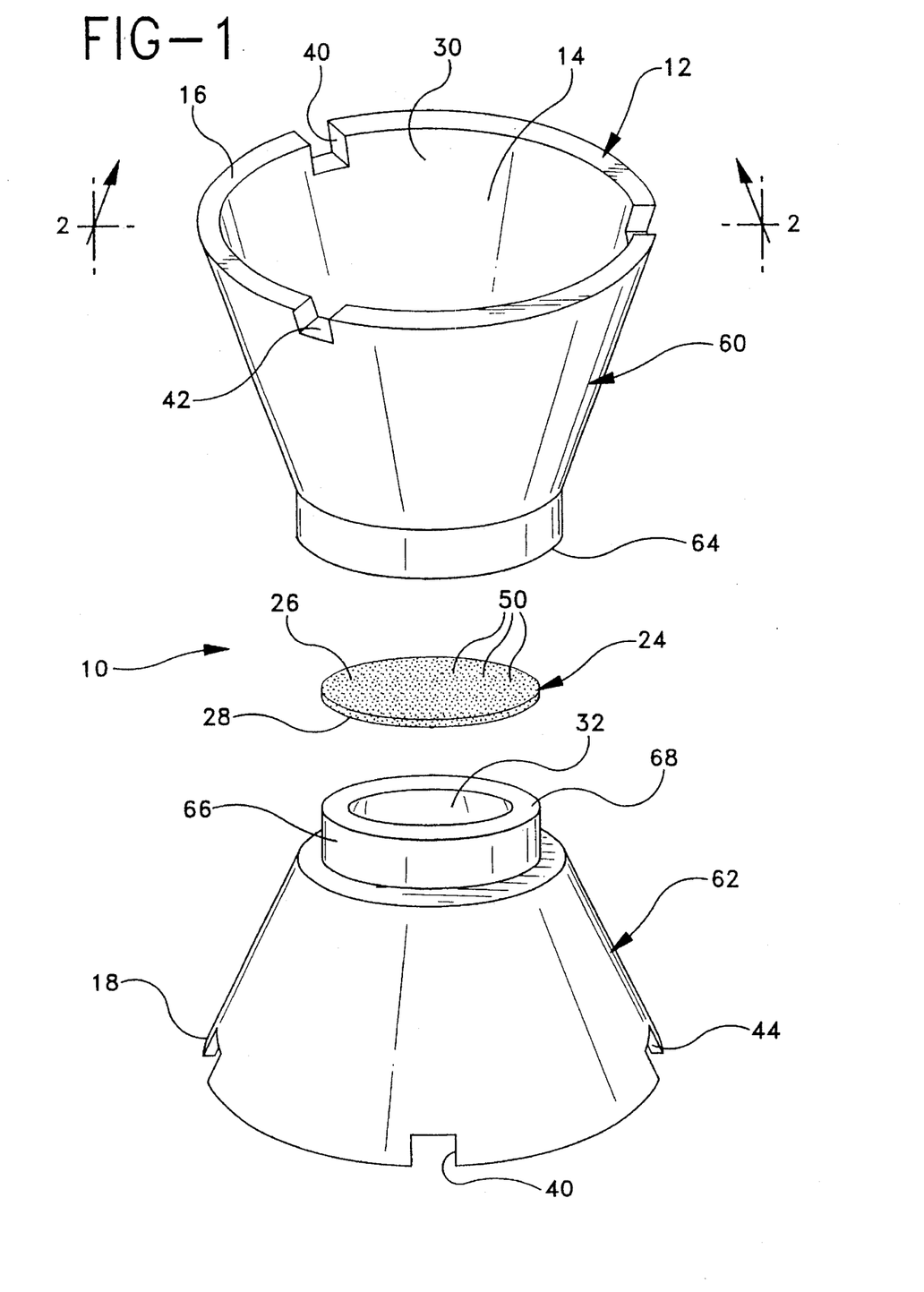
FIG. 1 is an exploded perspective representation of the preferred insert of the present invention.
Figure 2:
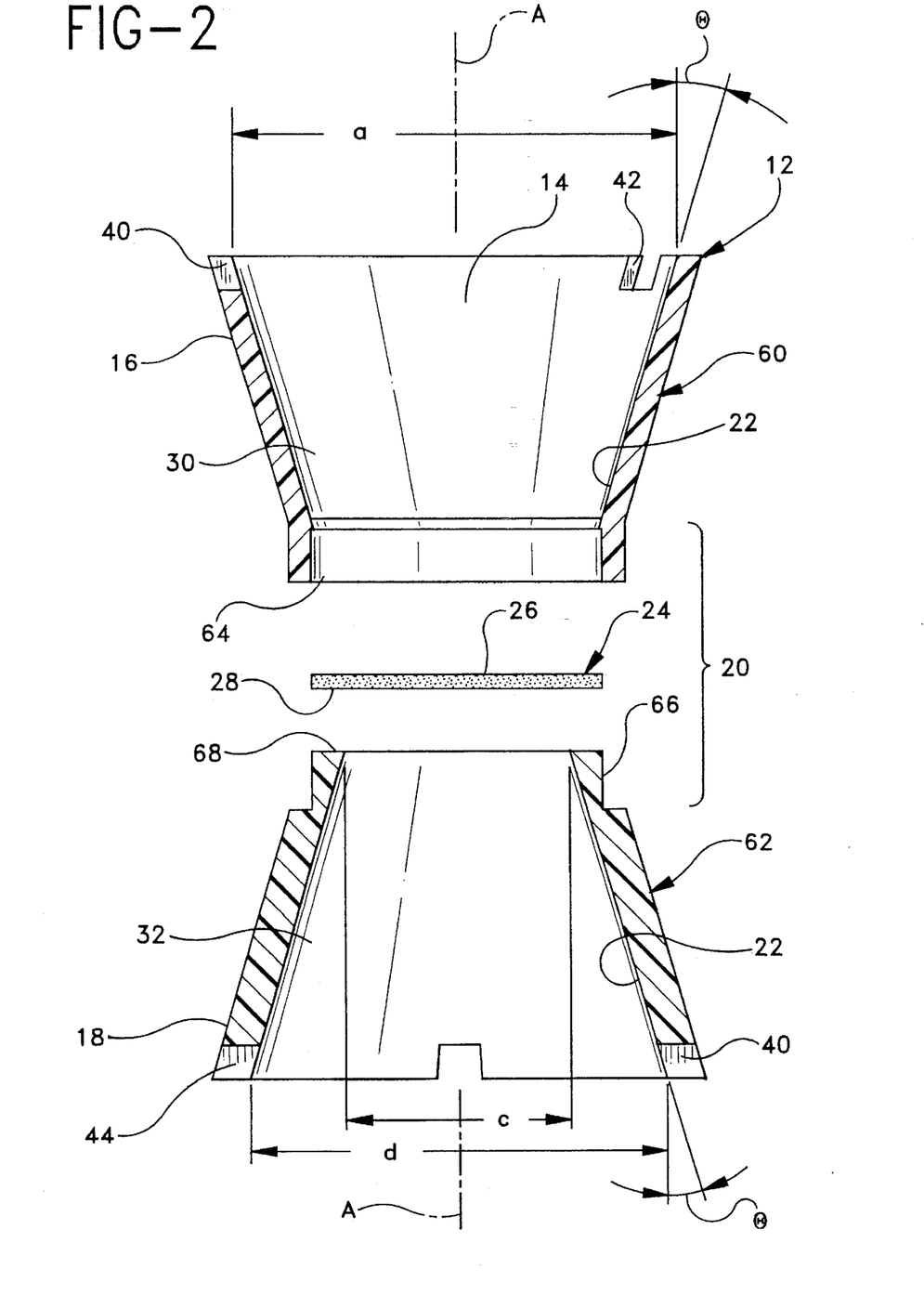
FIG. 2 is a schematic cross-section of the insert of the present invention as shown in FIG. 1 taken along the line 2—2.

The center section includes a porous membrane 24 with a first surface 26 toward first end 16 and a second surface 28 toward second end 18. Membrane 24 is preferably attached across and obstructs passageway 14. The membrane divides the passageway into a first receptacle 30 formed from passageway 14 by membrane first surface 26 toward first end 16 and a second receptacle 32 formed from passageway 14 by membrane second surface 28 toward second end 18.

Figure 3A:
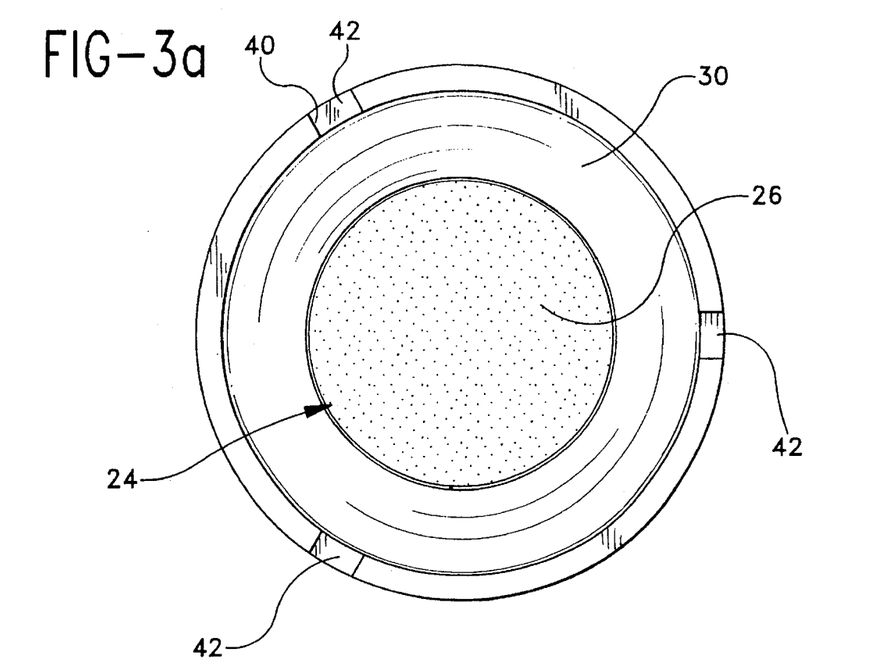
FIG. 3a is a plan view from the first end of the insert of the present invention as shown in FIG. 1.
Figure 3B:
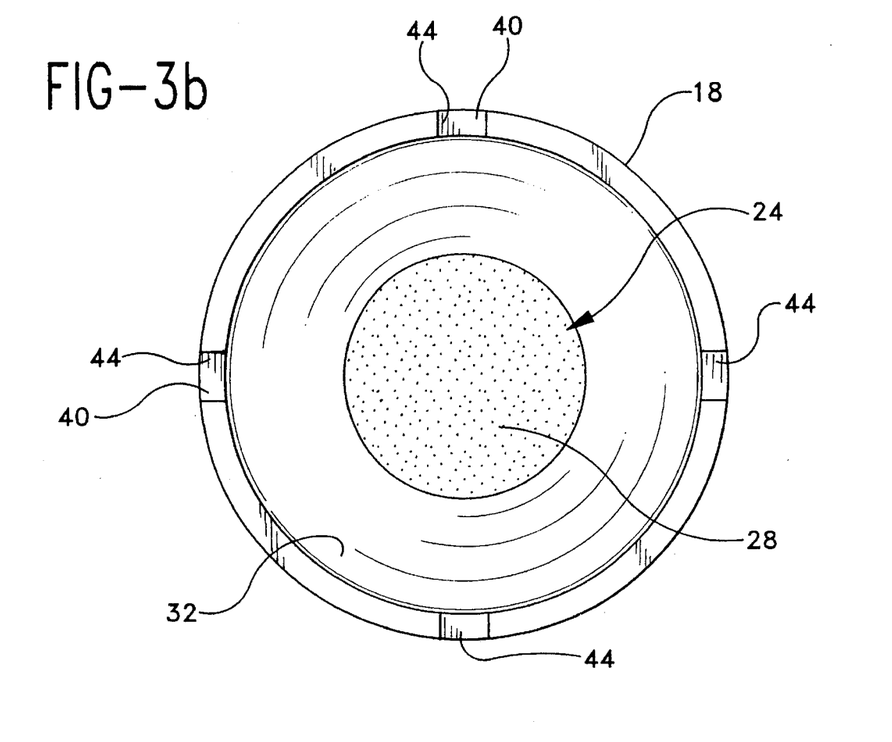
FIG. 3b is a plan view from the second end of the insert of the present invention as shown in FIG. 1.

Preferably first end 16 and second end 18 include crenellation 40 to allow fluid communication from inside the receptacles to an outside environment when insert 10 is upright and standing on one of the ends in a well containing growth medium. As is shown in FIGS. 3a and 3b, it is preferred that a crenellation pattern 42 at first end 16 differs from a crenellation pattern 44 at second end 18 thereby providing rapid visual identification of the first end and second end to allow differentiation between cells having similar physical appearance. The crenellation may be squared notches as shown in the Figs. or other shapes that allow fluid communication between the receptacles and the outside environment.

Preferably insert 10 of the present invention is formed in two portions, a first portion 60 and a second portion 62 joined at center section 20. Preferred first portion 60 includes a socket 64 for receiving the second portion. Preferably second portion 62 has a projection 66 sized to fit within socket 64 and form center section 20 of the insert. Projection 66 preferably includes an area 68 for mounting membrane 24 so that when the portions are joined to form the insert, projection 66 and socket 64 form center section 20 with membrane 24 substantially perpendicularly across passageway 14 intermediate the first and second end.

Preferably first portion 60 and second portion 62 are formed by an injection molding process from a thermoplastic resin. Suitable resins are polycarbonate, polyethyleneterephthalate, polystyrene, polyvinylchloride, polymethylmethacrylate and the like. Preferably the first portion and the second portion are formed from polyethyleneterephthalate.

Porous membrane 24 preferably is formed from a material such as polyethylene terephthalate, polycarbonate and the like with a multiplicity of open pores 50 therethrough. Preferably pores 50 have an inside diameter between about 0.2 microns to about 10.0 microns and membrane 24 preferably has a pore density between about $0.1 \times 10^6$ to about $10 \times 10^6$ pores per square centimeter. Most preferably, membrane 24 is formed from polyethyleneterephthalate having pores with a diameter of about 1 micron and a pore density about $1.6 \times 10^6$ pores per square centimeter.

Membrane 24 may be attached to area 68 by heat sealing, sonic welding, solvent bonding, adhesive bonding and the like. More preferably membrane 24 is affixed to area 68 by heat sealing. Alternatively, membrane 24 may be mechanically attached by entrapment between first portion 60 and second portion 62.

First portion 60 may be attached to second portion 62 by heat sealing, sonic welding, solvent bonding, adhesive bonding and the like. Alternately, first portion 60 may be attached to second portion 62 by a mechanical interference fit. Preferably, the first portion is attached to the second portion by sonic welding.

Taper 22 of passageway 14 between the first and second ends and the center section of the cell culture insert of the present invention forms a draft angle theta (Θ) between about two degrees to about forty-five degrees. Preferably, draft angle Θ is between about two degrees to about 15 degrees. The purpose of the taper is to allow substantially all entrapped air to escape from the receptacles when the insert is substantially horizontally submerged in liquid growth media. For the purpose of this description, the terms "horizontal" and "vertical" apply to an axis A of passageway 14 of the hollow housing.

Figure 4A:
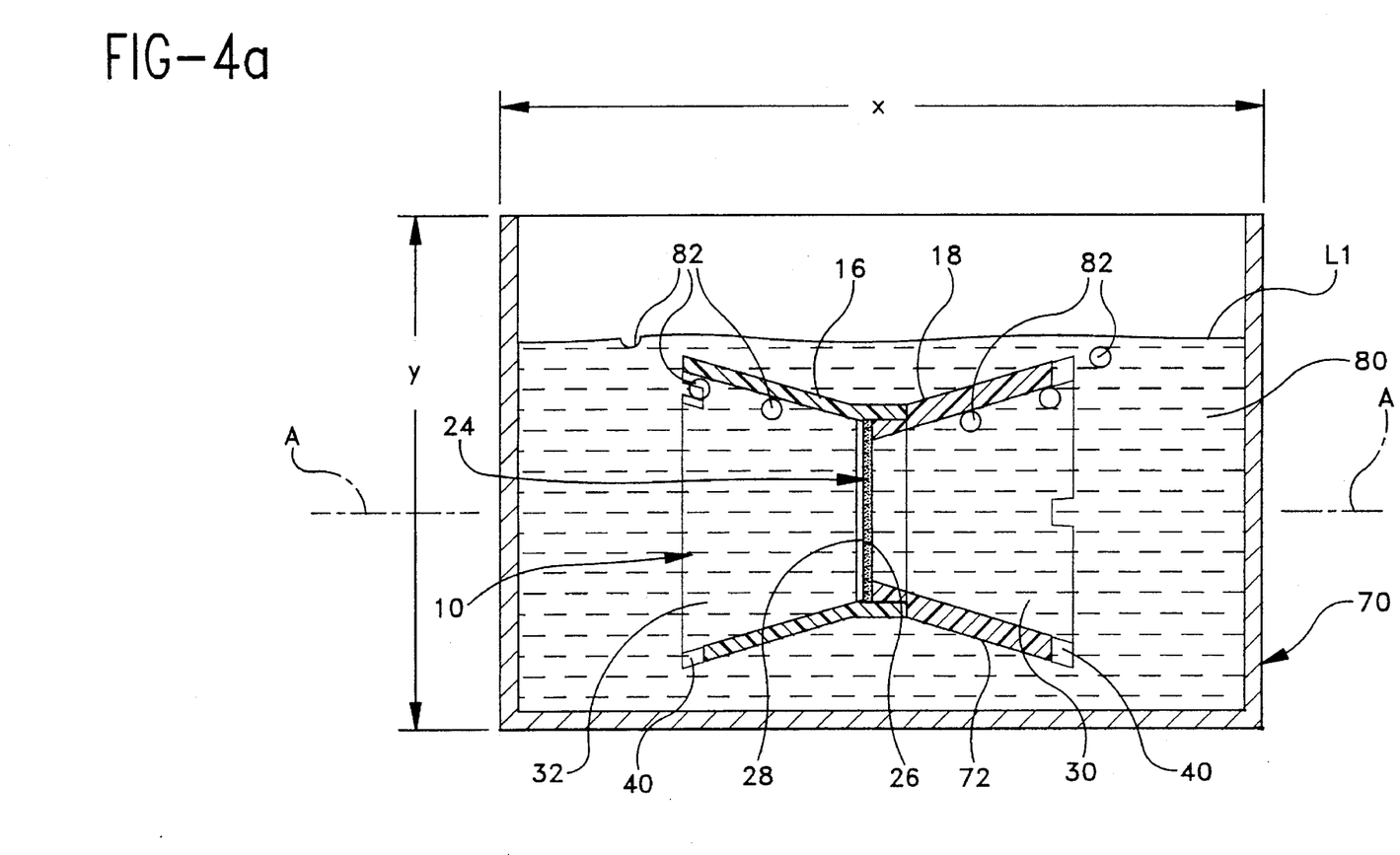
FIG. 4a is a schematic cross-sectional view of the insert of the present invention FIG. 1 immersed substantially horizontally in a well containing liquid cell growth medium.
Figure 4B:
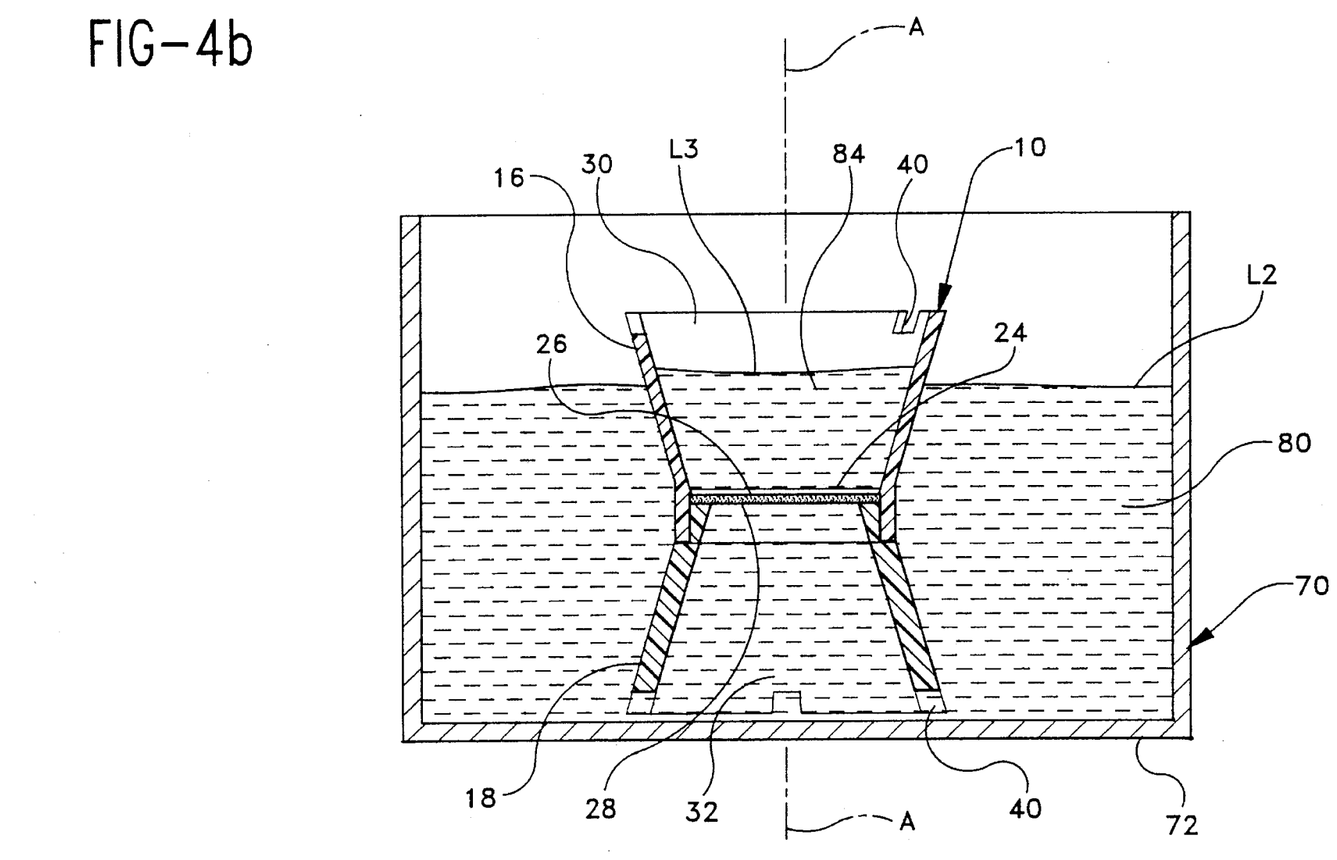
FIG. 4b is a schematic cross-sectional view of the insert of the present invention from in FIG. 1 standing substantially vertically in a well containing liquid cell growth medium.
Figure 5A:
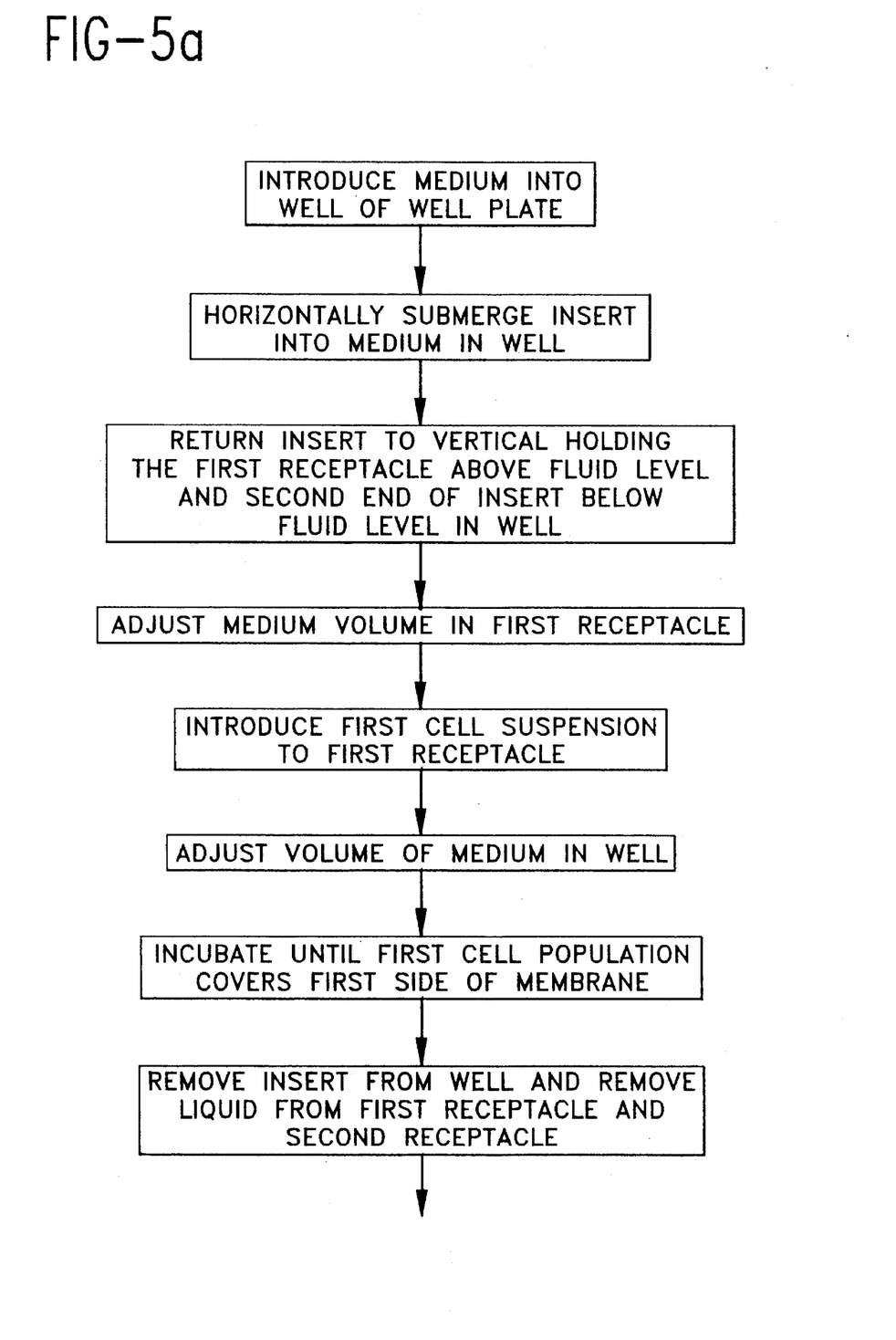
FIGS. 5a and 5b show a process flow chart of the preferred method of the present invention for culturing cells on both sides of a porous membrane.
Figure 5B:
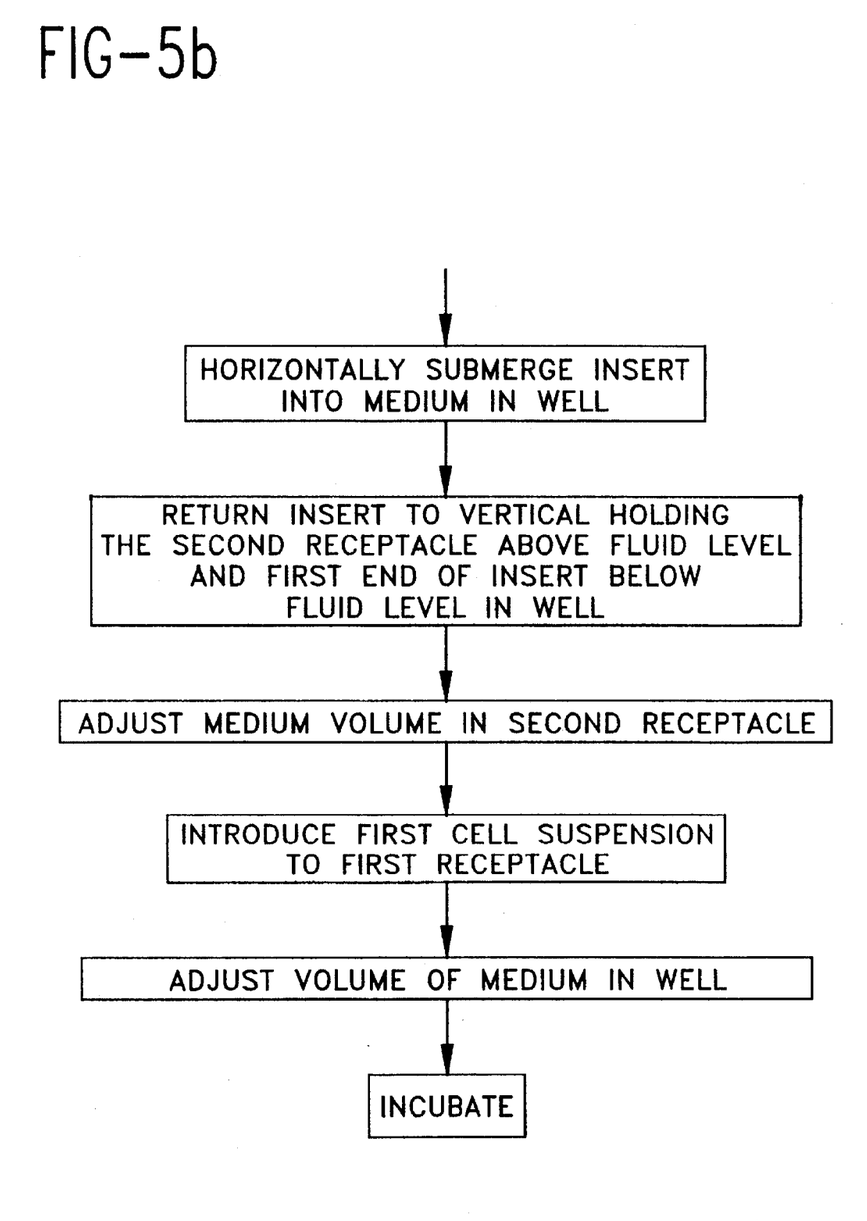

A preferred method for growing populations of cells on both sides of membrane 24 is schematically illustrated in FIGS. 4a and 4b, and displayed as a process flow chart in FIGS. 5a and 5b. The process flow chart is intended to be illustrative, not to be limitive of the preferred method of the present invention. For particular applications, it may be desirable to carry out the steps in a different order, and add or omit steps. The preferred method includes submerging the cell culture insert of the present invention 10 horizontally in a first well 70 having a depth "Y" with a width "X" and a bottom 72. Depth Y and width X should be sufficient to allow insert 10 to be covered in liquid growth medium 80 having an initial level $L_1$ to completely submerge the insert when the insert is substantially horizontal with the membrane being substantially perpendicular to axis A. When the insert is submerged in this fashion, the taper of the passageway allows substantially all air bubbles, illustrated as 82 in FIG. 4a to be displaced by the liquid medium and escape from the receptacles. Alternately, the insert may be only partially submerged with Axis A forming an acute angle with the liquid, leaving one receptacle out of the liquid medium, the submerged receptacle filling with the liquid and substantially displacing the air because of the tapered wall.

The preferred method includes tipping the insert to a substantially vertical position while maintaining second end 18 below the surface of the liquid and standing the insert substantially vertical on second end 18 on the bottom of the well thereby maintaining the second receptacle substantially liquid full. Preferably, the level of medium 80 in the well is then adjusted to a level $L_2$ so that the insert stands in the well. The level of medium $L_3$ in first receptacle 30 is then adjusted so that a sufficient volume for culturing cells is present.

Preferably, a first suspension of cells is then introduced into the first receptacle and the first well with the insert is then placed in a suitable environment for incubating the first cell culture and forming a growth of the first cells on first surface 26 of the porous membrane. Since second receptacle 32 is substantially liquid full, there are substantially no air bubbles on membrane second surface 28 to interfere to inhibit a substantially continuous growth of the first cells on first surface 26. Additionally, while insert 10 is standing on second end 18, crenellation 40 allows free fluid communication between liquid medium 80 and second receptacle 32.

When the cells of the first suspension develop the desired population, insert 10 is preferably removed from the well and drained, leaving the growth of first cells on first surface 26 of the membrane. Depending on the particular application, well 70 may be reused as for the purpose of simplification of this description, the recitation of the method for developing a second population of cells on second surface 28 of the membrane is not illustrated, but is described hereinbelow. All structural elements involved in the second population culture are fully identified and described above, and the placement of the insert in the well is analogous to the description and the Figs. for developing the population of cells on the first side of the membrane.

Insert 10 preferably is then substantially horizontally submerged in the well containing sufficient growth medium to cover the insert when the membrane is substantially perpendicular to Axis A and the receptacles fill with medium substantially displacing air bubbles. Preferably, the insert is tipped to a substantially vertical position while maintaining first end 16 below the surface of the liquid medium so that first receptacle 30 fills with medium and has substantially no air bubbles. Insert 10 is then preferably stood on first end 16 on bottom 72 of the well so that second receptacle 32 is upward. The medium level in the second receptacle is adjusted so that a sufficient volume for culturing cells is present and the medium level in the well is adjusted so the insert stands in the well.

Preferably, a second suspension of cells is introduced into the second receptacle and the well with the insert is placed in an environment suitable for incubation of both the cell populations and development of a population of cells from the second suspension on second side 28 of the membrane.

One skilled in the art of culturing cells and manipulating laboratory vessels will recognize that the level adjustments of medium in the receptacles and wells would likely be performed with pipettes or similar volumetric suction or delivery devices.

The insert of the present invention provides the practitioner of trans-membrane co-culture with a simple, easy-to-use device which, when used according to the preferred method of the present invention, provides populations of cells on both sides of a porous membrane. The invention facilitates studies of cellular interactions, cellular structure development, blood-brain barrier transport phenomenon as well as preparation of cellular products from one population of cells which require the presence of another population of cells. The insert of the present invention represents an advance over previously disclosed devices and methods by its simplicity and ease of use.

What is claimed is:

1. A trans-membrane co-culture insert comprising:
   a hollow housing having a passageway therethrough, a first end, a second end and a center section intermediate said first end and said second end;
   said passageway having an inside diameter at said first end and said second end, said inside diameters at each of said ends being greater than an inside diameter of said passageway at said center section so that said passageway forms a taper from each of said ends to said center section; and
   said center section further comprising a porous membrane having a first surface and a second surface, said membrane being attached across and obstructing said passageway thereby dividing said passageway into a first receptacle formed from said passageway by said membrane first surface toward said first end and a second receptacle formed from said passageway by said membrane second surface toward said second end; and
   said first end and said second end each including at least one opening therein, said openings allowing fluid communication from inside said receptacles to an outside environment when said housing is standing on said first or second end and wherein said first end openings differ from said second end openings thereby distinguishing said first end from said second end.

2. The insert of claim 1 wherein said inside diameters of said passageway at said first and said second ends are substantially equal.

3. The insert of claim 1 wherein said porous membrane is formed from a material selected from the group consisting of polyethyleneterephthalate and polycarbonate, said membrane having open pores therethrough having a diameter between about 0.2 to about 10.0 microns and a pore density between about $0.1 \times 10^6$ to about $10.0 \times 10^6$ pores per square centimeter.

4. The insert of claim 3 wherein said porous membrane is formed from polyethyleneterephthalate having pores with a diameter about 1 micron and a pore density about $1.6 \times 10^6$ pores per square centimeter.

5. The insert of claim 1 wherein said insert is formed from a first portion and a second portion, said portions being attached at said center section;

said first portion having a socket for receiving said second portion, said second portion having a projection sized to fit within said socket, said projection further including an area for mounting said membrane thereon, so that when said portions are joined to form said insert, said projection and said socket form said center section with said membrane substantially perpendicular across said passageway intermediate said first end and said second end.

6. The insert of claim 5 wherein said membrane is attached to said area by a method selected from the group consisting of heat sealing, sonic welding, solvent bonding and adhesive bonding and mechanic entrapment between said first portion and said second portion.

7. The insert of claim 6 wherein said first portion is attached to said second portion by a method selected from the group consisting of heat sealing, sonic welding, solvent bonding, mechanical interference fit and adhesive bonding.

8. The insert of claim 5 wherein said first portion and said second portion are formed from a thermoplastic resin selected from the group consisting of polycarbonate, polyethyleneterephthalate, polystyrene, polyvinylchloride and polymethylmethacrylate.

9. The insert of claim 8 wherein said first portion and said second portion are formed from polyethyleneterephthalate.

10. The insert of claim 1 wherein said taper of said passageway has a draft angle from said ends to said center section between about 2 degrees to about 45 degrees.

11. The insert of claim 10 wherein said draft angle is between about 2 degrees and about 15 degrees.

12. A trans-membrane co-culture insert comprising:

a hollow housing with a passageway therethrough having a first end, a second end and a center section intermediate said first end and said second end;

said passageway having substantially equal inside diameters at said first end and said second end, said inside diameters at each of said ends being greater than an inside diameter of said center section so that said passageway forms a taper from each of said ends to said center section, said first end and said second end further each including at least one opening therein, said openings allowing fluid communication from inside said receptacles to an outside environment when said housing is standing on said first or second end and wherein said first end openings differ from said second end openings thereby distinguishing said first end from said second end;

said center section further including a porous membrane having a first surface and a second surface, said membrane being perpendicularly across and obstructing said passageway so that a first receptacle is formed from said passageway by said membrane first surface toward said first end and a second receptacle is formed from said passageway by said membrane second surface toward said second end;

said housing being formed from a first portion and a second portion, said portions being attached at said center section;

said first portion having a socket for receiving said second portion, said second portion having a projection sized to fit within said socket, said projection further including an area for mounting said membrane thereon, so that when said sections are joined to form said insert, said projection and said socket form said center section; and said membrane being fixedly attached to said area by heat sealing and said second portion being bonded to said first portion by a sonic welding process.

13. The insert of claim 12 wherein said porous membrane is formed from a material selected from the group consisting of polyethylene terephthalate and polycarbonate, said membrane having open pores therethrough having a diameter about 1.0 micron and a pore density about $1.6 \times 10^6$ pores per square centimeter.

14. The insert of claim 12 wherein said taper of said passageway has a draft angle from said ends to said center section between about 2 degrees and about 15 degrees.

15. A method for growing cells on both sides of a porous membrane comprises:

submerging a cell culture insert comprising a hollow housing having an axial passageway therethrough, a first end, a second end and a center section intermediate said first end and said second end, said passageway having an inside diameter at said first end and said second end, said inside diameters at each of said ends being greater than an inside diameter of said passageway at said center section so that said passageway forms a taper from each of said ends to said center section, and said center section further comprising a porous membrane having a first surface and a second surface, said membrane being attached across and obstructing said passageway thereby dividing said passageway into a first receptacle formed from said passageway by said membrane first surface toward said first end and a second receptacle formed from said passageway by said membrane second surface toward said second end horizontally in a well, the well having a bottom and containing sufficient liquid cell growth medium to submerge the insert substantially horizontally with respect to said axis, so that the membrane is substantially vertical and the medium displaces the air in the receptacle;

tipping the insert to a substantially vertical position while maintaining the second end below the surface of the medium so that the second receptacle is filled with medium and has no air bubbles;

standing the insert on its second end in the well so that the first receptacle of the membrane is upward;

adjusting the volume of medium in the first receptacle so that a sufficient volume for culturing cells is present;

adjusting the volume of medium in the well so that the insert stands in the well;

introducing a first cell culture suspension in the first receptacle;

incubating the well with the insert therein so that the first cell culture forms a growth on the first surface of the membrane;

removing the insert from the well;

draining the first receptacle leaving the first cell growth on the first surface;

submerging the insert substantially horizontally in a well, the well containing sufficient liquid cell growth medium to submerge the insert horizontally, so that the membrane is substantially vertical and the receptacles fill with the medium without air bubbles;

tipping the insert to a vertical position while maintaining the first end below the surface of the medium so that the first receptacle is filled with medium and has no air bubbles;

standing the insert on its first end in the well so that the second receptacle is upward;

adjusting the volume of medium in the second receptacle so that a sufficient volume for culturing cells is present;

adjusting the volume of medium in the well so that the insert stands in the well;

introducing a second cell culture suspension in the second receptacle; and incubating the well with the insert therein so that the second cell culture forms a growth on the second surface of the membrane.

* * * * *